(12) United States Patent
Hodd et al.

(10) Patent No.: US 7,141,248 B2
(45) Date of Patent: Nov. 28, 2006

(54) METHODS OF PRODUCING INTRAOCULAR LENSES

(75) Inventors: Kenneth A. Hodd, Wrexham (GB); Keith Alfred Dillingham, Groningen (NL); Jacqueline de Groot, Leek (NL)

(73) Assignee: AMO Groningen BV, Groningen (NL)

( * ) Notice: Subject to any disclaimer, the term of this patent is extended or adjusted under 35 U.S.C. 154(b) by 449 days.

(21) Appl. No.: 10/444,268

(22) Filed: May 23, 2003

(65) Prior Publication Data
US 2004/0037867 A1    Feb. 26, 2004

Related U.S. Application Data

(62) Division of application No. 09/623,577, filed as application No. PCT/EP99/01766 on Mar. 16, 1999, now Pat. No. 6,589,550.

(30) Foreign Application Priority Data
Mar. 16, 1998   (SE)   .................... 9800853

(51) Int. Cl.
*A61F 2/00*    (2006.01)
(52) U.S. Cl. ..................... 424/427; D24/157
(58) Field of Classification Search ............... None
See application file for complete search history.

(56) References Cited

U.S. PATENT DOCUMENTS

| | | | | |
|---|---|---|---|---|
| 3,920,810 A | * | 11/1975 | Rankin ................. 424/78.04 |
| 4,347,198 A | * | 8/1982 | Ohkada et al. ............. 264/2.3 |
| 4,542,542 A | | 9/1985 | Wright |
| 4,680,336 A | * | 7/1987 | Larsen et al. ............... 524/548 |
| 4,787,904 A | | 11/1988 | Severin et al. |
| 4,859,719 A | * | 8/1989 | Ofstead ..................... 523/108 |
| 5,120,121 A | * | 6/1992 | Rawlings et al. ........... 351/162 |
| 5,147,394 A | * | 9/1992 | Siepser et al. ............... 623/6.6 |
| 5,224,957 A | | 7/1993 | Gasser et al. |
| 5,665,840 A | | 9/1997 | Phlmann et al. |
| 5,945,498 A | | 8/1999 | Hopkin et al. |
| 6,015,842 A | | 1/2000 | LeBoeuf et al. |
| 6,589,550 B1 | * | 7/2003 | Hodd et al. ................ 424/429 |
| 6,861,065 B1 | * | 3/2005 | Hodd et al. ................ 424/427 |

FOREIGN PATENT DOCUMENTS

| | | |
|---|---|---|
| EP | 0414219 | 2/1993 |
| GB | 2090264 | 12/1981 |
| WO | 9302639 | 2/1993 |
| WO | 9624074 | 8/1996 |
| WO | WO 9624074 | 8/1996 |

OTHER PUBLICATIONS

Graham et al., Nanogels and Microgels: The new polymeric materials playground, *Pure & Appl. Chem.*, vol. 70, No. 6, pp. 1271-1275, 1998.
Fisher, The Elastic Constants of the Human Lens, *J. Physiol.* (1971), 212, pp. 147-180.
Van Alphen et al., Elasticity of Tissues Involved In Accommodation, *Vision Res.* vol. 31, No. 7/8, pp. 1417-1438, 1991.

* cited by examiner

Primary Examiner—Gollamudi S. Kishore
Assistant Examiner—Pili A. Hawes
(74) Attorney, Agent, or Firm—Dinsmore & Shohl LLP

(57) ABSTRACT

Methods of producing an intraocular lens include introducing a solution into a lens forming enclosure, wherein the solution comprises discrete crosslinkable units of a size small enough to provide an optically clear solution while contributing to a high refractive index of at least 1.3, performing crosslinking between the units of the solution, and thereby forming a solid lens in the enclosure, optionally under a forming pressure.

15 Claims, No Drawings

METHODS OF PRODUCING INTRAOCULAR LENSES

RELATED APPLICATION

The present application is a divisional of U.S. application Ser. No. 09/623,577 filed Oct. 25, 2000, now U.S. Pat. No. 6,589,550 which is a 371 of PCT/EP99/01766 filed Mar. 16, 1999.

FIELD OF INVENTION

The present invention relates to the field of intraocular lenses (IOLs) and in particular to new lens materials as well as to methods of producing accommodating lenses based on these materials in vivo, which means that the lens is formed in the capsular bag of the eye.

BACKGROUND OF THE INVENTION

When an ophthalmic surgeon operates on a cataract (s)he replaces the defective natural lens with a small artificial lens, an IOL. In order to remove the natural, cataractous lens, as well as to prepare for the introduction of the IOL, an incision must be made into the eye. For many years most of the IOLs were made of poly(methylmethacrylate), a material with good optical characteristics and compatibility with tissues in the eye. A disadvantage of PMMA is, however, that it is a very rigid material and the incision must be made big enough, at least 5–6 mm, for implantation of the lens. With improved devices for removal of the natural lens by phacoemulsification, requiring only a rather small incision, there was a need for lenses with deformable optics. This intended property can be achieved, for instance, by making lenses which are foldable or can be dried to a reduced size, but which swells to its original shape in the eye. Various silicone or hydrogel based lenses have been suggested and in some cases also commercialized. In such small incision surgery an opening of only 3–4 mm is required.

The implantation of lenses of the types mentioned above necessitates the patient using spectacle correction for reading. More recently, to overcome this limitation of the conventional IOL, increasing attention has been given to refractive, as well as diffractive, bifocal or multifocal lenses. The use of such lenses is increasing slowly, but as they introduce an optical deficiency in patients, a reduced perception of contrast, which becomes more acute in twilight, their widespread application may be limited.

Even with the mentioned types of improved implantable IOLs, available on the market, there is still a desire to obtain a lens for which is required an even smaller incision and which behaves like the natural lens in the eye, i.e. to be accommodating, with a focal point which is regulated by action of the ciliary muscle in the eye. In order to allow for a really small incision it would be necessary to form the lens inside the eye from a solution which is injected into the capsular bag or into a balloon placed inside the bag. Lenses formed from an injected solution of monomers have already been suggested in the literature and are based on a technique in which the natural lens is removed and, after cleaning of the capsular bag, a polymerizable composition is injected into the bag, whereupon the solution is polymerized, e.g. after initiation by light of suitable wavelength, using the form of the capsular bag as the mold. Thin walled inflatable balloons of silicone rubber have also been developed which can be inserted into the capsular bag and filled with the desired polymer system.

Most researchers of the development of the accommodative re-fill lens have used silicone based systems for filling the capsular bag, either in the form of silicone oils or low temperature vulcanizing (LTV) silicone elastomers. Such systems suffer from disadvantages in the context of re-fill lens formation: the dimethyl silicones have a restricted refractive index (1.40), LTVs cure slowly, up to 12 hours may be needed to complete their setting and their slow setting may result in material leakage out of the capsular bag through the surgical incision. In order to overcome this problem, U.S. Pat. No. 4,542,542 discloses such a silicon based injected system which is partially cured by heat in the vicinity of the injection hole of the capsular bag to effect a first sealing effect. It is a further complication that the high viscosities of some silicone oils and intermediates make their air-bubble free injection very difficult.

Hettlich et al (German J Ophthalmol (1992) 1 p. 346–349) were among the first to propose the use of photopolymerization of a monomer system as an alternative approach to setting the material within the capsular bag. He pointed to the clinical success of blue light photocurable resins for dental applications and explored the use of such systems as injectible materials for filling capsular bags. The systems used by Hettlich et al. were effective in demonstrating the efficacy of blue light photocurable resins for filling capsular bags. Another example of an injectible system is described in EP 414219, in which the liquid composition comprises a difunctional acrylate and or methacrylate ester and a photoinitiator activatable by light of wavelength 400–500 nm. By choosing an initiator of such high wavelength the presence of a UV absorber, which is desired to be present in the final lens in order to protect the retina from damage, does not create a problem.

Unfortunately, the in vivo polymerizable systems described so far do not solve all the problems involved with this interesting and potentially very useful concept, as e.g. leakage of monomers and initiator from the bag into the surrounding parts of the eye between injection and polymerization might occur. With increasing polymerization time such leakage might be substantial and cause serious complications. Another disadvantage observed in systems of the type described above is shrinkage of the material during polymerization with the formation of a lens which does not completely fill up the capsular bag. Further, the systems used have formed materials with moduli too high to allow accommodative processes. The natural lens of the eye is a material with extremely low modulus, in the general range 1–5 kPa, which can be compared to glassy plastics with a modulus of six orders of magnitude greater. PMMA as mentioned above has a value around 3000 MPa.

It would consequently be highly desirable to be able to obtain an ophthalmically acceptable solution which could be injected into the capsular bag of the eye with a conventional cannula after the natural lens has been surgically removed and that such a solution could be subjected to a process that would result in the production of an intraocular lens capable of functionally replace the natural lens, while avoiding the above-mentioned problems. In particular, such a solution must be water based and in a simple manner capable of being reacted into a gel formed solid lens material. It has earlier been described in U.S. Pat. No. 5,665,840 how to produce contact lenses from a water soluble crosslinkable pre-polymer. The production involves a photoinitiator which is activated by UV-light to produce crosslinking reaction to the gel formed lens material. In this publication it is not considered how to inject a water based solution into the capsular bag for lens production and arrive with a lens of a suitable modulus.

It is obvious that several technical problems remain before a method of producing an intraocular lens from injecting a water based aqueous solution directly into the capsular bag can be accomplished in a sufficiently safe and reproductive manner. As earlier mentioned, it would be preferable to start from a material that is already polymerized in order to avoid free monomers, although an aqueous solution of sufficiently low viscosity to be injected through standard syringe equipment must be used for the purpose of minimizing the incision of the capsular bag.

It is also a requirement that the material should have a suitably high refractive index to generate a lens with sufficient optic power and quality and the material shall be able to be cured in a controlled manner by visible light to a lens product with sufficiently low elasticity (modulus) resembling that of the natural lens. Consequently, it is a further requirement to involve a photoinitiator, capable of inducing a curing reaction of the material in aqueous solution which is substantially free from clinical hazards.

The present invention aims to solve the mentioned problems by providing novel methods of producing intraocular lenses and an aqueous solution serving as an injectible starting material for the production.

DESCRIPTION OF THE INVENTION

The present invention refers to a method of producing an intraocular lens wherein a solution is introduced into a lens forming enclosure. The solution comprises discrete crosslinkable units of a size small enough to provide an optically clear solution while contributing to a high refractive index of at least 1.39. In the lens forming enclosure a crosslinking reaction is performed between the units of the solution in order to form a solid lens, optionally under forming pressure. It is a highly preferred aspect of the present invention that the crosslinking reaction between the units is initiated by exposing a photoinitiator to light of a suitable wavelength and that the photoinitiator is soluble in the solution and present therein. In this method it is preferred that the discrete crosslinkable units are macromolecular particles having functional groups capable of forming crosslinks between the particles so as to form the lens. The crosslinking reactions preferably are induced by light in the visible or UV spectrum. More preferably, the light has wavelength above 305 nm and most preferably in the range of 380 to 700 nm.

The macromolecular particles are preferably prepared from controlled polymerization reaction, as will be explained below in greater detail, from monomers with suitable characteristics for an ophthalmic device, such as being contributory to a product with a suitable refractive index and clinical safety.

The inventive method can be applied to produce intraocular lenses with a wide variety of properties both in a conventional mold or, as explained below, directly in the capsular bag of the eye. Conventional rigid lenses, semi rigid or flexible foldable lenses can be prepared, as well as elastically deformable lenses with properties to restore the accommodation of the patient. For elastically deformable lenses it is highly preferred that the modulus of the produced lens material is within the range of 0.1 to 20 kPa since it can be expected that such lenses can be accommodated under the influence of the ciliary muscles of the eye. It is also a requirement that any lens production in-vivo employs an aqueous solution for introduction into the capsular bag with so low viscosity that it can be conveniently be injected into the eye with standard means. In all these applications, it is of considerable advantage to be able to provide a solution for production which comprises crosslinkable units compared to a solution of monomers, since it will be possible to overcome any subsequent contraction of the material which is a drawback with existing techniques with monomer solutions.

According to a preferred embodiment, the present invention refers to a method of producing an intraocular lens in vivo, i.e. directly in the human eye. The method includes the preparation of a composition of discrete water soluble macromolecular particles and mixing such a composition with a water soluble photoinitiator to an ophthalmically acceptable aqueous solution having a refractive index of at least 1.39. The method further includes injection of the resultant aqueous solution into the capsular bag of the eye and initiation of crosslinking between said macromolecular particles by irradiation with light of a wavelength in the range of about 380 to 700 nm to create a lens in the capsular bag.

It is of particular importance that the inventive methods arrive with a resultant lens material of a controlled modulus which is similar to the modulus of the natural crystal lens.

The inventive methods are equally suitable for production of a lens in-vivo in the human eye as in molds suitable for conventional lens production.

The present invention also includes an ophthalmically acceptable aqueous solution designed to accomplish the above mentioned inventive methods.

It is an important feature of the aqueous solution that it comprises discrete crosslinkable units of a size small enough to provide an optically clear solution. It is a also a requirement that the aqueous solution has a sufficiently low viscosity to be injected with a conventional cannula into the capsular bag of the eye wherein the natural lens has been removed with a surgical process. It is a further requirement that the aqueous solution has a sufficiently high refractive index so that the resultant lens product has a refractive index of about 1.39 to 1.46. Preferably, the lens should have a refractive index of about 1.41 to be a suitable replacement of the natural lens. It is therefore desirable that the aqueous solution of crosslinkable units has a refractive index above about 1.39 already before crosslinking takes place.

In order to comply with requirements of optical clarity, low viscosity and a high refractive index, the aqueous solution of the present invention comprises water soluble macromolecular particles of a controlled size and molecular weight which can undergo crosslinking to the final product. Suitably, the diameters of the macromolecular particles are in the range of between about 5 to 160 nm, preferably about 10 to 150 nm and more preferably about 20 to 100 nm. Preferably, the molecular weight of the particles are at least 50 000 Daltons.

Accordingly, it is one of the key features of the invention to use macromolecular particles instead of monomers, or long chains of conventional polymer molecules, as suggested in prior art, for creating the polymeric structure of the lens. By using a solution of macromolecular particles, it is possible to obtain a suitably low viscosity so the solution can be injected by a conventional thin cannula, while the solution has a sufficient particle concentration to obtain a high refractive index. To obtain a low viscosity solution with conventional linear polymers would be a considerable technical problem without compromising with the polymer concentration and thereby the refractive index of the lens product. Another considerable advantage with the low viscosity solutions of macromolecular particles according to the present invention is their high mobility which for example enable accurate filling of the lens production enclosure, if necessary by adjustments.

In order to obtain a suitably high refractive index, it is therefore preferred that the solutions according to the present invention comprise at least about 35% (w/w) of the discreet crosslinkable units (i.e. macromolecular particles and suitably in a range from about 35 to 50% (w/w). If increasing the number units, the refractive index and the viscosity of the solution will accordingly increase. It is too be understood that the skilled will be able to find a suitable compromise between these parameters and arrive with solutions suitable for practicing the inventive methods.

Further by using macromolecular particles as the basic unit for subsequent crosslinking, the process in which the final lens is formed, the desired refractive index can be reached by selecting a high concentration of a suitable monomer contributing to this characteristic when forming the particles. The fact that the particles are formed prior to injection outside the eye, also result in a high degree of freedom to chose the best reaction conditions.

The skilled person can prepare different types of water soluble macromolecular particles for the inventive purposes by following different preparation routes. It is to be understood that within the context of the present invention different types of macromolecular particles can be prepared with different methods and monomer sources. The most important features of the macromolecular particles are that they include units or monomers which contribute to a high refractive index and that they include a sufficient amount of functional groups to be involved in the crosslinking to the final product. Further, the particles must include a sufficient amount of hydrophilic units or monomers to obtain suitable water solubility characteristics. Generally, these characteristics can be obtained with various types of particles including microgels or nanogels, dendrimers, nanospheres or particles having a core-shell structure such that the shell is hydrophilic and the core is hydrophobic. The skilled person has the knowledge of numerous different methods to provide such particles including methods of preparation in solution and by emulsion polymerization methods. Dependent on the production method and the constituents of the particle a number of methods are also known to the skilled person of how to collect the particles, purify them and bring them into an aqueous solution.

Preferably, the macromolecular particles include at least one hydrophilic group (repeating unit) and at least one group must contribute to a high refractive index of the solution of the particles, i.e. such groups preferably consist of a compound which when polymerized provides a material of high refractive index. The hydrophilic group and the high refractive index can be the same or different. Suitable hydrophilic units for the macromolecular particles are found among vinyl lactams and acrylamides. Vinyl lactams may generally be defined as a vinyl unit bound to a heterocyclic unit through its heterocyclic nitrogen atom, wherein said heterocyclic unit consists of 5 to 7 seven atoms and has carboxy group neighboring said bond. Some examples of vinyl lactams are N-vinyl-2-pyrrolidone, N-vinyl-2-piperidone and N-vinyl-caprolactam. Such vinyl lactams may be substituted with one or several lower alkyl groups.

An especially suitable vinyl lactam is N-vinylpyrrolidone and an especially suitable acrylamide is N,N-dimethylacrylamide. An especially suitable group to add as units in the macromolecular particles is N-benzyl-N-methylacrylamide for the purpose of increasing the refractive index of the product.

The macromolecular particles can further comprise a crosslinking agent which contributes to form crosslinking units in the internal polymeric network in the particles. An example of such a crosslinking agent is disclosed below in a specific system where a microgel like composition is discussed.

It is also an important aspect of the present invention that the macromolecular particles comprise units having functional groups suitable for crosslinking the particles into a solid elastically deformable lens. Preferably, the functional groups are selected from vinylic, acrylic or methacrylic groups.

The functional groups can be introduced according to different routes and chemical design. According to one embodiment the functional groups are introduced by means of complementary units in the particles to the above mentioned hydrophilic units. The functional groups may either be directly present on the complementary units or be introduced by further chemical modification of the particles. According to an alternative embodiment, the above mentioned crosslinking agent, necessary for creating crosslinking units within the polymeric network of the particles, can carry a sufficient amount of free functional groups for further crosslinking between the particles in order to create the final lens material.

One preferred route to introduce the functional groups to the particles is to add vinylic units to the mentioned hydrophilic units in the particle network. The vinylic units have groups for attaching the functional vinylic, acrylic or methacrylic groups for crosslinking selected among hydroxy groups, epoxy groups, carboxylic anhydride groups, lactone groups and isocyanate groups. Vinylic units suitable for this purpose can be selected from one or several of 2-hydroxyethylacrylate, 2-hydroxyethylmethacrylate, 2-aminohydroxyethylacrylate, 2-aminoethylacrylate, 2-aminoethylmethacrylate, glycidylacrylate and glycidylmethacrylate units. It is to be understood that the skilled person can find many different alternatives to the exemplified vinylic units with groups suitable for introducing the mentioned functional groups for crosslinking.

According to a preferred embodiment, the vinylic units are vinyl alcohol units formed by ester-exchange of vinyl acetate units. The so formed vinyl alcohol units are further chemically modified according to standard procedures for the introduction of a suitable amount of functional groups for crosslinking. For a reference of how to introduce this type of functional groups for crosslinking from vinyl acetate as a co-monomer of a pre-polymer, it is referred to the aforementioned U.S. Pat. No. 5,665,840.

An preferred composition of the macromolecular particles is a) vinyl lactam and/or acryl amide units;

b) vinylic units comprising functional groups selected among vinyl, acrylate and methacrylate groups; and c) crosslinking units providing internal crosslinking of the particles.

In a typical composition, the macromolecular particles comprise:

a) N-vinylpyrrolidone and/or N,N-dimethylacrylamide units in an amount of at least 50 w/w %;

b) vinyl alcohol units having functional groups for crosslinking; and c) crosslinking units.

Furthermore, as complement, the solutions of macromolecular particles referred to above can also comprise one or several monomers which will undergo copolymerization with the macromolecular particles when producing the lens material. For this aspect of the invention, the solution of macromolecular particles can either be aqueous or based on monomer solution and the photoinitiator must be adapted to be soluble in the monomer. As mentioned above, it is preferable to employ the inventive method in a mold when the alternative a monomer containing solution is used. It is also to be understood that the complementary monomers are selected from agents that contribute to specifically desired properties of produced lens, such as a suitable refractive index.

Additionally, the solutions referred to comprise further components necessary for producing lenses, such as UV absorbers, stabilizers and other agents used in common ophthalmologic practice.

Macromolecular particles can for example be produced with a solution polymerization method as disclosed by N. B Graham et al. in Pure & Appl. Chem., 1998, Vol. 70(6), pp. 1271–5 which is herewith incorporated as a reference. For the purposes of the present invention, these methods are modified to prepare water soluble macromolecular particles of the type of internally crosslinked hydrophilic particles, frequently referred to in the literature as microgels or nanogels. In this type of microgels the polymer molecules are constrained by the internal crosslinks to a spherical structure which prevents chain entanglement, which would otherwise increase the modulus of the formed lens. The precise dimensions of the microgel macromolecular particles are controlled by the conditions of their preparation and the swelling induced by the solvent in which they are dissolved. Typically, the diameters of the microgel spheres are in the range 5–160 nm. For the purposes of the present invention, it is of importance that the macromolecular particles comprise units of at least one hydrophilic group and one group with a high refractive index. Monomers having these characteristic must consequently be a substantial part of the starting material for the microgel production. Furthermore a crosslinking agent must be employed for the internal crosslinking of these particle units.

Suitable compositions of microgels include at least 50% weight of hydrophilic monomers and 1 to 50% (weight) of remaining monomer constituents and crosslinking agents. The remaining monomers referred to are selected according the discussion above regarding additional vinyl units for introducing functional groups for subsequent crosslinking of the particles and/or by their capacity to contribute to a high refractive index. The skilled person would accordingly be able to arrive with a different compositions given the conditions that particles must have high overall hydrophilic characteristics, contribute to an aqueous solution of a high refractive index and a have functional groups available for crosslinking.

A preferred microgel composition for injection is based on poly(N-vinylpyrrolidone) and copolymers of polyvinylpyrrolidone with a refractive index above about 1.5.

Vinylpyrrolidone copolymer microgels (VPCMs) can typically be prepared in a range of compositions by copolymerizing N-vinylpyrrolidone (VP), in mole fractions from 0.95 to 0.50, with vinylacetate (VAc), 2-hydroxyethylmethacrylate or another suitable monomer in mole fractions from 0.05 to 0.50, respectively, and a crosslinking monomer (a crosslinker providing internal crosslinking units in the particles), such as, diethylene glycol dimethacrylate, DEGDMA (0.05 moles). $\alpha,\alpha'$-Azobisisobutyronitrile (in concentrations varying from 0.05 to 3 weight-%) can be used as an initiator. Preferably the copolymerization process is heated, using combined monomer concentrations in the range 5 to 25 weight-%, in a better than theta solvent at 50 to 80° C. for up to 24 hours. In a better than theta solvent the difference in solubility parameter between the solvent and the polymer is less than about 2 $MPa^{1/2}$. For combinations of VP and VAc, solvents of suitable solubility parameters for the preparation of microgels are formed by mixing acetone and ethanol in molar proportions of acetone: ethanol, from 0.7 to 0.4; 0.3 to 0.6, respectively, which gives solubility parameters in the range 22 to 23 $MPa^{1/2}$.

For the subsequent crosslinking to take place in the eye, the microgel is prepared to contain a controlled amount of active (crosslinkable) sites, e.g. reactive vinyl groups. Since the modulus or rigidity of the lens is directly related to the degree of crosslinking the number of such reactive sites per polymer particle is critical for making accommodating lenses. The degree of crosslinking should preferably be in the range of 0.1 to 1.0, involving volume fractions of microgel from 0.1 to 0.5, based on total composition, i.e. the balance will derive from water in combination with linear polymers, etc., as required to meet the restrictions imposed on concentration by the need to meet a specific refractive index of 1.39 to 1.46.

In addition to the water soluble crosslinkable macromolecular particles, the ophthalmically acceptable aqueous solution to be used for intraocular lens production preferably includes a water soluble photoinitiator. The photoinitiator should preferably be capable of initiating crosslinking of the particles into a solid elastically deformable gel upon exposure of light of a wavelength exceeding about 305 nm.

It is an important object of the present invention that such a water soluble photoinitiator should remain locked into the resultant lens material it contributes to generate. This minimizes any physiological hazards from molecular fragments originating from the photoinitiator regardless of its initial concentration. Therefore, it is preferable that the photoinitiator residues subsequent to crosslinking form an integral part of the network constituting the intraocular lens material. In order to accomplish this feature, the photoinitiator comprises at least one photoactive compound attached to a water soluble macromolecule. According to a preferred embodiment, the photoinitiator comprises photoactive groups attached to linear polymers. Alternatively, the photoinitiator comprises photoactive groups attached to macromolecular particles. It is to be understood that the macromolecule carriers of the photoinitiator are compatible with the macromolecular material constituting the particles. Therefore, it is preferred that they comprise hydrophilic units such as N-vinyl pyrrolidone, acryl amides and other suitable water solubilizing monomers, such as vinylmorpholine. Photoinitiators of this preferred type can be referred to as photocrosslinkers, since they provide a combination of photoinitiating and crosslinking reactions wherein they ultimately form a part of the network forming the resultant material.

It is suitable that the photoactive group is selected from acyl- and/or aroyl-phosphine oxides. In particular, the photoactive group comprises an aroyl group selected from a group consisting of 4-carbonylphenylene, 3,5-dimethoxy-4-carbonylphenylene, 3,5-dimethylol-4-carbonylphenylene and 3,5-dimethyl-4-carbonylphenylene. Typically preferred photoactive groups are 4-vinylbenzoyldiphenyl-phosphine oxide and 4-vinyl-1,6-dimethylbenzoyldiphenyl-phosphine oxide.

An important feature of the preferred photoinitiators having photoactive compounds attached to suitable hydrophilic polymeric carriers is that they have a capacity to, when irradiated by light, act as crosslinkers for the crosslinkable macromolecular particles. The remaining photoinitiators will thereby form a part of the network constituting the lens material or be safely locked within said network.

It is preferable that the highly reactive ophthalmically acceptable aqueous solution is prepared just prior to the injection. For this reason the present invention includes the provision of a kit-of-parts for preparing the ophthalmically acceptable solution comprising a composition of water soluble discrete crosslinkable units, a composition of a water soluble photoinitiator and means for bringing the compositions together into said aqueous solution for suitable subsequent injection. It is to be understood that any of the composition of crosslinkable units or the composition of the photoinitiator may be in dehydrated form during storage for stability reasons and would need reconstitution into an aqueous solution. The kit for preparing the final aqueous solution can therefore optionally further include a fluid in the form of an aqueous composition for dissolving such a composition and reconstitute it for injection. It is also to be understood that any of the compositions of the kit can include additional agents, such as conventional stabilizers or preservatives and agents contributing to the characteristics of the final lens product, such as UV-absorbers. It is further to be understood that the kit-of-parts can be designed according to conventional principles in the pharmaceutical industry and thereby using conventional methods for protecting the kit from light of wavelengths that may trigger the reactivity of the photoinitiator. The purpose of the design of the kit is that it should be delivered as an article which is ready to use for the ophthalmic surgeon. For example, in its simplest form it may comprise different containers with mixing instruction or it may consist of an injection device capable of operating on a multi-chamber ampoule containing the stored precursors to the ophthalmically acceptable aqueous solution in different chambers. The skilled person is aware of several such suitable devices, see for example European Patent No. 0298067.

The methods according to the present invention comprise a metered introduction of a high refractive index, low viscosity solution into an enclosure for forming an intraocular lens with subsequent crosslinking, optionally under a forming pressure, wherein the solution comprises crosslinkable macromolecular particles and a soluble photoinitiator. The macromolecular particles are chosen so that they after crosslinking contribute to reproduce the optical performance of the natural lens, which means a final refractive index close to 1.41, preferably in the range of 1.39 to 1.46.

Preferably, a high refractive index, low viscosity, ophthalmically acceptable aqueous solution is injected directly into the capsular bag of the human eye. The lens formed from crosslinking the particles of the solution, therefore preferably must have the optical and mechanical characteristics necessary for the restoration of accommodation, i.e. the formed lens must be able to accommodate under the action of the ciliary muscle. The (elasticity) modulus of the material of the human crystalline lens has been measured with different techniques in different test groups by RF Fisher in J Physiol., 1971, 212; pp. 147–180 and G W Alphen et al. in Vision Res., 1991, 31, pp. 1417–1438. From these studies it can be concluded that the variations in modulus of the human lens is within the range of about 0.1 to 20 kPa. To respond to the accommodating forces the compression characteristics of the resulting lens therefore will have to be precisely controlled and be very reproducible, with a compressive modulus in the range of from about 0.1 to 20 kPa, preferably 0.1 to 10 kPa and most preferably from about 1 to 5 kPa.

By selecting appropriate compositions, as outlined in the present invention, it is possible to control the degree of crosslinking in the final reaction and thereby control the modulus of the produced intraocular lens. This can for example be accomplished by selecting appropriate materials in the crosslinkable units, by introducing a suitable number of functional groups for crosslinking in the crosslinkable units or by selecting suitable concentrations of the constituents of the injectible solution. Accordingly, by means of the methods and the compositions provided by the present invention it is possible to obtain a high degree of freedom in selecting a suitable lens modulus for patient and replicate the modulus of a lens in a person around 40 years or younger.

The following examples aim to demonstrate a route to perform the present invention which is not limited in scope to the specific embodiments disclosed therein.

DETAILED AND EXEMPLIFYING PART OF THE DESCRIPTION

It has been demonstrated in the British Patent Specification 2090264 that the selection of solvent has a critical influence in the preparation of microgels with respect to their formation and position of the gelation boundary. The following examples are illustrative of the production of water soluble microgels of differing molecular weights for the same monomer proportions in different solvents (compare Examples 1 and 3) and the use of different monomer combinations (compare Examples 2 and 4).

Example 1

Vinylacetate (VAc) (10 w/w %, 0.20 g, 2.3 mmol), diethylene-glycol divinylether (DEGDVE) (5 w/w %, 0.10 g, 0.63 mmol), N-vinylpyrrolidone (NVP) (85 w/w %, 1.7 g, 15.3 mmol) were dissolved in methanol (3.71 g, 4.69 ml) to give 35 w/w % solution. The solution was poured into a Wheaton serum bottle and azo-isobutyronitrile (AIBN, 0.060 g, 3 w/w % of total monomers) was added. The bottle was sealed, shaken for 2 min. and placed in an oven at 60° C. and the reaction mixture was heated for 24 hours. Upon cooling the solution from the reaction, the resulting microgel was precipitated with ether, collected by filtration and dried in a vacuum oven at room temperature. The yield was 1.92 g (96%) and colorless microgel particles were soluble in water, ethanol and methanol. The weight average molar mass ($M_w$) of this product, when curve fitted and averaged was 280 000 D. $M_w$ was measured by SEC/MALS (size exclusion chromatography with multi-angel light scattering).

Example 2

The preparative method described in Example 1 was repeated in 50 w/w % solution of ethanol (2.00 g, 2.52 ml) instead of methanol 35 w/w %. The product was worked up as described previously in Example 1 and the yield was 1.85 g (about 93%) of colorless microgel particles which were soluble in water, ethanol and methanol. The weight average molar mass ($M_w$) of this product, when curve fitted and averaged was 500 000 D. Mw was measured by SEC/MALS.

Example 3

The preparative method described in Example 1 was repeated in 50 w/w % solution of butane-2-one (2.00 g, 4.48 ml) instead of methanol 35 w/w %. The product was worked up as described previously in Example 1 and the yield was 1.90 g (95%) of having a bimodal weight average molar mass (Mw), when curve fitted and averaged, a first peak of 25 200 D and a second peak of 5 257 000 D were identified. Mw:s were measured by SEC/MALS.

Example 4

N,N-dimethylacrylamide (DMA), (6.40 g, 57 mmol), 2-hydroxyethyl methacrylate (HEMA), (0.80 g, 6.2 mmol) and ethyleneglycol dimethacrylate (EGDMA), (0.80 g, 4.0 mmol) were weighed to a pressure flask, AIBN (azo-bisisobutyronitrile) (0.20 g, 0.25 w/w monomers %) into ethanol was added, and the volume made up to 100 ml with ethanol (monomer concentration 8 w/v %). The flask was flushed with $N_2$, and heated at 60° C. for 24 h. The product from the reaction was precipitated with hexane, the precipitate dissolved in tetrahydrofuran, reprecipitated with ether and vacuum desiccated to constituent weight. The yield 5.46 g (68%) of white microgel particles which were soluble in water, alcohol, tetrahydrofuran, and chloroform. SEC-MALS showed a Mw of this microgel (using a curve-fitted average) to be $2.69 \times 10^6$ D and the average particle diameter to be 70 nm. A 35 w/w % (38 w/v %) solution of the microgel in water was a colorless liquid with refractive index 1.395 and viscosity 730 cSt, both measured at 25° C. H-NMR analysis suggested that DMA, HEMA and EGDMA had entered the polymer in close to stoichiometric ratio.

Example 5

Using the method described in Example 4 with DMA (7.20 g, 64 mmol), HEMA (1.08 g, 8.3 mmol), EGDMA (0.72 g, 3.6 mmol) and AIBN (0.023 g, 0.26 w/w monomers %) dissolved in ethanol to give a 9 w monomers/v % solution. The product was microgel (5.71 g, 63% yield), having a $M_w$ of $2.47 \times 10^5$ D, and an average particle diameter of 144 nm (both by SEC/MALS analysis, as previously). This product was soluble in water and some other common solvents giving mobile colorless solutions.

Example 6

Using the method described in Example 4 with DMA (7.20 g, 64 mmol), HEMA (0.99 g, 7.6 mmol), EGDMA (0.81 g, 4.1 mmol) and AIBN (0.023 g, 0.26 w/w monomers %) dissolved in ethanol to give a 9 w monomers/v % solution. The product was microgel (5.12 g, 57% yield), having a $M_w$ of $2.68 \times 10^7$ D, and an average particle diameter of 138 nm (both by SEC/MALS analysis, as previously). This product was soluble in water and some other common solvents giving mobile colorless solutions.

Example 7

A mixture of the monomers was prepared: 75 parts N,N-dimethylacrylamide (DMA), 10 parts N-benzyl-N-methylacrylamide, (BMA), 5 parts 2-hydroxyethyl methacrylate (HEMA), and 10 parts ethyleneglycol dimethacrylate (EGDMA), by weight, and 2.8 g of the mixture was placed in a 50 ml penicillin bottle. Azo-bisisobutyronitrile, 7 mg in ethanolic solution, was added, and the volume made up to 35 ml with ethanol, thus 8 w/v % monomers. The vessel was purged with nitrogen, septum sealed, and heated 22 h at 60° C., after which the clear solution was poured to ether, and the product reprecipitated from ethanol. The vacuum dried yield was 1.06 g (38%) of white polymer. H-NMR analysis showed a molar ratio: 7.4/92.6 BMA/DMA. The refractive index of a 35 w/w % solution was 1.396 at 25° C.

Example 8

Modification of NVP/VAc microgel by ester exchange.

Microgel (10 g), containing VAc units (12.5 mmol) prepared in a manner similar to Example 1, was dissolved in methanol (100 ml) and to the resulting solution was added a solution of sodium hydroxide (0.36 g, 9 mmol) in water (3 ml). The microgel solution was stirred and heated at 40° C. for 24 h. The resulting solution of modified microgel was dialyzed versus water for 48 h and the methanol and water were removed by evaporation in a rotary evaporator at ambient temperature and dried thoroughly in a vacuum oven at 40° C. The IR spectrum of the recovered microgel indicated that the conversion of acetate to hydroxyl groups was about 90%.

Example 9

Using microgel (10 g, approximately 12.5 mmol VAc repeating units) prepared in a manner similar to Example 2, the ester-exchange reaction described in Example 8 was repeated. IR analysis revealed that the product was again about 90% converted (acetate to alcohol).

Example 10

Further modification of NVP/VAc microgel introducing vinyl groups serving as functional groups for crosslinking between the particles.

Microgel product from Example 9 (5.0 g, containing approximately 11 mmol of vinyl alcohol units) was dissolved in dimethylacetamide (DMAc, 45 ml) and triethylamine (TEA, 0.81 g, 8.1 mmol) was added to the solution while stirring. Methacroyl chloride (MACl, 1.1 g, 10.5 mmol) was next added very slowly, dropwise, with continued stirring at room temperature. Stirring of the reaction mixture was continued for a further 24 h at 40° C. in the dark.

The reaction solution was diluted with DMAc (50 ml) and poured into an excess of acetone (1.5 l) to precipitate the vinylated microgel. This was collected at the pump, washed thoroughly with acetone and dried in vacuo at room temperature. The NMR spectrum indicated 3–5 mol % vinyl groups.

Example 11

Microgel prepared in accordance with Example 4 (6.01 g) was dissolved in 58 ml DMAc and treated as in Example 10. Acryloyl chloride (2.03 g) was added and mixture and resulting product was treated as in Example 10 with a yield of 5.20 g. NMR analysis showed vinyl peaks in molar ratio of 0.10/0.90 acryl groups/DMA units.

Example 12

Microgel product from Example 4 (5.0 g) was weighed to a adried flask and dissolved in N,N-dimethylacetamide 48 ml. Methacroyl chloride (MACl, 2.05 g) was added and the mixture heated in a bath at 40° C. for 18 h. the clear colorless solution resulting was poured into hexane, and the product taken up in absolute alcohol and repreciated to diethyl ether, before drying under vacuum at room temperature. The yield was 4.13 g of white polymer. In aqueous solution, the product decolorized bromine water. H-NMR analysis showed polymeric vinyl peaks (d 6.13 and 5.60 ppm) in molar ratio 0.11/0.89 methacryl groups/DMA units.

Example 13

The viscosity and refractive index were tested herein for concentrated solutions of microgels suitable for preparation of ophthalmically acceptable aqueous liquids for lens production.

The application of microgel systems to the molding an of an artificial crystalline lens (ACL) requires the injection of a concentrated aqueous (saline) solution of the microgel through a standard cannula into the capsular bag of the eye. The Table below gives examples that illustrate that aqueous microgel solutions have suitable viscosities and refractive indices (selected) for ACL applications.

| Microgel Composition (w/w %) | Viscosity (cSt) | Injection thro' 18 gauge cannula (Y/N) | Refractive Index (w/H20 v %) |
|---|---|---|---|
| NVP(55)/VAc(40)/DEGDVE(5) | 180–250 | Y | 1.39(33) |
| NVP(90)/VAc(5)/DEGDVE(5) | <180 | Y | 1.39(31) |
| DMA(80)/HEMA(10)/EGDMA(10) | 730 | Y | 1.395(38) |

Example 14

0.300 g Microgel modified with functional vinyl groups for crosslinking in accordance with Example 11 was weighed into a vial and 0.704 g water was added. On standing, the microgel was dissolved to a clear colorless solution. A photoinitiator for starting the crosslinking was added to the solution (0.102 g) and the mixture was warmed to dissolve. The photoinitiator comprises a photoactive linear polymer of a copolymer of N.N-dimethylacrylamide containing 2.0 mol % of photoactive units derived from 1,6-dimethylbenzoylphosphine oxide. An aliquot of the mixture was easily dispensed through 18 gauge needle to a Teflon disk and covered with a glass slide. On 2 minutes irradiation with blue light (source: Vivadent Heliolux DLX dental gun emitting 400–525 nm), the mixture formed a tack-free gel.

Example 15

Microgel prepared according to Example 11, was dissolved in water to give a 35 w/w % solution. An aliquot of this solution, 358 mg, was mixed with 58 mg of a 25 w/w % solution of the same photoinitiator as in Example 11 and 175 mg of the mixture was transferred through an 18 gauge hypodermic cannula to a Teflon disk. On irradiating with blue light (source: Vivadent Heliolux DLX dental gun, emitting 400–525 nm) for 20 seconds, a transparent gel with elastic properties was formed.

The invention claimed is:

1. A method of producing an intraocular lens including: (i) introducing a solution into a lens forming enclosure, said solution comprising discrete crosslinkable units comprising macromolecular particles of a size small enough to provide an optically clear solution while contributing to a high refractive index of at least 1.39; (ii) performing crosslinking between said units of the solution; and thereby (iii) forming a solid lens in said enclosure, optionally under a forming pressure.

2. A method according to claim 1 wherein said crosslinking is initiated by exposing a photoinitiator which is soluble in said solution to light.

3. A method according to claim 2, wherein said crosslinkable units are macromolecular particles having a size range between about 20 to 160 nm.

4. A method according claim 2, wherein said solution has a sufficiently low viscosity to be injected with a conventional cannula into said forming enclosure.

5. A method according to claim 1, wherein the formed lens is an elastically deformable lens with a modulus in the range of about 0.1 to 20 kPa.

6. A method according to claim 2, wherein said crosslinking reaction is initiated by light of a wavelength above about 305 nm.

7. A method according to claim 4, wherein said solution is an ophthalmically acceptable aqueous solution.

8. A method according to claim 7 wherein the aqueous solution comprises a water soluble photoinitiator.

9. A method according to claim 8, wherein the soluble photoinitiator comprises at least one photoactive compound attached to a water soluble macromolecule.

10. A method according to claim 3, wherein said macromolecular particles are provided with functional groups for crosslinking.

11. A method according to claim 10, wherein the functional groups comprise vinylic, acrylic or methacrylic groups.

12. A method according to claim 10, wherein the macromolecular particles are water soluble.

13. A method according to claim 12, wherein the macromolecular particles comprise units derived from vinyl lactams and/or acrylamides, of which at least one unit contributes to provide a solution of the particles with a refractive index of at least 1.39 and at least one unit contributes to provide the particles with hydrophilic overall characteristics.

14. A method according to claim 13, wherein said vinyl lactam is N-vinylpyrrolidone.

15. A method according to claim 13, wherein said acrylamide is N,N-dimethylacrylamide.

* * * * *